(12) United States Patent
Liu et al.

(10) Patent No.: US 9,096,487 B2
(45) Date of Patent: Aug. 4, 2015

(54) ALKYLATION METHOD USING IONIC LIQUID AS CATALYST

(75) Inventors: Zhichang Liu, Beijing (CN); Chunming Xu, Beijing (CN); Rui Zhang, Beijing (CN); Xianghai Meng, Beijing (CN)

(73) Assignee: Shell Oil Company, Houston, TX (US)

(*) Notice: Subject to any disclaimer, the term of this patent is extended or adjusted under 35 U.S.C. 154(b) by 652 days.

(21) Appl. No.: 13/519,191

(22) PCT Filed: Dec. 27, 2010

(86) PCT No.: PCT/CN2010/002173
§ 371 (c)(1),
(2), (4) Date: Jun. 18, 2013

(87) PCT Pub. No.: WO2011/079516
PCT Pub. Date: Jul. 7, 2011

(65) Prior Publication Data
US 2013/0331625 A1 Dec. 12, 2013

(30) Foreign Application Priority Data
Dec. 28, 2009 (CN) .......................... 2009 1 0244097

(51) Int. Cl.
*C07C 2/60* (2006.01)
*C07C 2/58* (2006.01)
*B01J 31/02* (2006.01)
*C10G 29/20* (2006.01)
*C10G 57/00* (2006.01)

(52) U.S. Cl.
CPC .............. *C07C 2/58* (2013.01); *B01J 31/0278* (2013.01); *B01J 31/0284* (2013.01); *C10G 29/205* (2013.01); *C10G 57/005* (2013.01); *B01J 2231/42* (2013.01); *C10G 2300/1081* (2013.01); *C10G 2300/1092* (2013.01); *C10G 2300/4081* (2013.01); *C10G 2300/70* (2013.01)

(58) Field of Classification Search
USPC ........................................ 585/712, 722, 729
See application file for complete search history.

(56) References Cited

U.S. PATENT DOCUMENTS

| 7,285,698 | B2 | 10/2007 | Liu et al. .................. 585/721 |
|---|---|---|---|
| 7,732,363 | B2 | 6/2010 | Elomari et al. ............... 502/20 |
| 7,737,067 | B2 | 6/2010 | Elomari et al. ............... 502/28 |
| 2004/0133056 | A1 | 7/2004 | Liu et al. .................. 585/721 |
| 2007/0142211 | A1 | 6/2007 | Elomari et al. ............... 502/29 |
| 2007/0142214 | A1 | 6/2007 | Elomari et al. ............... 502/53 |
| 2009/0163750 | A1 | 6/2009 | Timken et al. ............... 585/312 |
| 2009/0163759 | A1 | 6/2009 | Driver et al. ............... 585/826 |
| 2009/0171133 | A1 | 7/2009 | Luo et al. .................... 585/14 |

FOREIGN PATENT DOCUMENTS

| CN | 1500764 | 6/2004 | ............... C07C 2/58 |
|---|---|---|---|
| CN | 101234945 | 8/2008 | ............... C07C 2/58 |
| WO | WO2007112238 | 10/2007 | ............... C07C 2/58 |
| WO | WO2008076722 | 6/2008 | ............... C07C 2/56 |

*Primary Examiner* — Thuan D Dang (57) ABSTRACT

Disclosed is an alkylation process using ionic liquid as catalyst, which process comprises separating halogenated hydrocarbons-rich fraction from the alkylation product by distillation and/or adsorption and reintroducing the separated fraction into the reaction system during the alkylation reaction, wherein the ionic liquid catalyst used in the alkylation reaction has a cation derived from hydrohalide of alkyl amine, hydrohalide of imidazole or hydrohalide of pyridine and an anion derived from one or more metallic compounds. The inventive process effectively utilizes the halogenated hydrocarbons in the alkylation product, prolongs the life of the ionic liquid catalyst, and reduces the halogen content in the alkylate oil.

12 Claims, 4 Drawing Sheets

ALKYLATION METHOD USING IONIC LIQUID AS CATALYST

PRIORITY CLAIM

The present application claims priority from PCT/CN2010/002173, filed 27 Dec. 2010, which claims priority from CN 200910244097.X, filed 28 Dec. 2009.

FIELD OF THE INVENTION

The present invention is related to a catalytic alkylation process for producing alkylate oil using ionic liquid as catalyst. The present invention belongs to the petrochemical field.

BACKGROUND OF THE INVENTION

In petroleum refining industry, the alkylation reaction between isobutane and butene (also referred as C4 alkylation or isobutane alkylation) is an important process for producing clean high-octane gasoline blending component. It has been known that the catalyst used in the alkylation reaction may comprise hydrofluoric acid, concentrated sulfuric acid and ionic liquids, wherein hydrofluoric acid and concentrated sulfuric acid are conventional industrial catalysts for this process. Both of hydrofluoric acid and concentrated sulfuric acid exhibit satisfactory properties in terms of activity, selectivity and catalyst lifetime, however, they may result in some problems such as environmental pollution, equipments corrosion as well as personnel injuries etc., thus, the industrial development of C4 alkylation being limited seriously.

As a novel compound system, ionic liquids have the properties such as being environmental friendly, less corrosive, low toxicity, adjustable acidity and physical-chemical properties, being easily separated from the product as well as being recycled at high rate, so that to become a novel desired catalytic material to be used for C4 alkylation instead of those liquid strong acids such as hydrofluoric acid and concentrated sulfuric acid. U.S. Pat. No. 7,285,698 and CN 1500764A respectively disclosed the catalytic processes for the alkylation reaction between isobutane and butene using a composite ionic liquid as catalyst, wherein the yield of the alkylation product—alkylate oil may be up to 170-180% by volume of the alkene feed, C8 fraction may constitute 60-80% of the alkylate oil, most prominently trimethylpentane may be more than 70% of C8 fraction, and RON (Research Octane Number) may be of 93-98.

More and more researches have been made on the ionic liquids regarding their properties and utilizations due to their multiple benefits as catalysts. However, the researchers have found that there are still some practical difficulties to be overcome when the ionic liquids being used as catalysts in the alkylation reaction. No matter the simple ionic liquid, of which the anion is derived from a single metallic compound, or the composite ionic liquid is used as the catalyst in the catalytic alkylation reaction, the catalyst will get deactivated inevitably. The feed amount processed by per gram of the ionic liquid catalyst can hardly be more than 100 g, thus, the ionic liquid catalyst had to be replaced and regenerated frequently and the corresponding industrial process would be limited apparently. There are also some researches providing technical solutions based on the believed reasons why the ionic liquid catalyst getting deactivated. For example, Chinese patent application 200710063459.6 disclosed a process for prolonging the catalyst life by using metallic aluminum or aluminum trichloride as aluminum source to compensate the aluminum trichloride lost due to entrainment in oil phase and hydrolysis of ionic liquid in the presence of water. The inventors of this application have found that the primary reason for chloroaluminate as ionic liquid catalyst getting deactivated is the loss of the active aluminum trichloride therein decreases the reaction activity, and the loss of aluminum trichloride is primarily due to the hydrolysis of aluminum trichloride caused by the inevitable water in the reaction feed and further possibly due to that aluminum trichloride may be entrained into oil phase due to complexation with some strong electron-donating species, which may be present in the reaction system. Thus, said patent application provided a process for producing alkylate oil, wherein the ionic liquid catalyst is regenerated on line continuously by using metallic aluminum or aluminum trichloride as aluminum source to compensate the aluminum trichloride lost due to entrainment in oil phase and hydrolysis of ionic liquid so as to makeup aluminum continuously and extend the catalyst life. Said patent application further stated that the process can also reduce the amount of HCl present in the catalytic reaction system, thus maintaining the selectivity of the targeted isooctane in the product at high level and reducing the corrosion due to the presence of HCl. However, a series of patent documents such as Chinese patent application CN 200680051282.1, CN 200680052353.X, United States Patents USP 20070142211 and USP 20070142214 disclosed processes for regenerating ionic liquid catalysts used in alkylation reaction by removing mixed polymers therefrom because it is believed that the ionic liquid catalysts get deactivated due to their anionic components being deactivated by the mixed polymers.

Therefore, it is very important to effectively overcome the deactivation of the ionic liquids in order to develop and promote their uses as commercial catalysts for producing alkylate oil.

SUMMARY OF THE INVENTION

The major technical problem to be solved by the present invention is to provide an alkylation process using ionic liquid as catalyst, the process, based on the mechanism of catalytic alkylation reaction by an acidic ionic liquid and by reintroducing halogenated hydrocarbons-rich fraction into the reaction system, can effectively prolong the life of the acidic ionic liquid catalyst and reduce the halogenated hydrocarbon content in the alkylate oil product simultaneously.

To this end, the present invention provides an alkylation process for producing alkylate oil using ionic liquid as catalyst, wherein during the alkylation reaction the reaction feed is a mixture of C4 alkene and C4 alkane with C4 alkane being at an excessive amount and then separated from the alkylation product and recycled, and the process further comprises separating halogenated hydrocarbons-rich fraction from the alkylation product and reintroducing the separated fraction into the reaction system during the alkylation reaction, and the ionic liquid catalyst used in the alkylation reaction has a cation derived from hydrohalide of alkyl amine, hydrohalide of imidazole or hydrohalide of pyridine and an anion derived from one or more metallic compounds.

The catalytic alkylation reaction by ionic liquid is following the positively charged carbon ion mechanism, wherein both Lewis acid and Brönsted acid (also referred as B acid) of the ionic liquid function together during the catalytic reaction. Based on the researches, the present inventors have found that when the ionic liquid catalyst is selected from the components comprising halide, the acidity of Brönsted acid in the ionic liquid is provided mainly by the hydrogen halide. During the catalytic alkylation reaction by the ionic liquid, the hydrogen halide as an auxiliary agent is reacted with C4 alkene to produce halogenated hydrocarbons, which are the intermediate of the positively charged carbon ion during the initial reaction phase. It can be seen that if the produced halogenated hydrocarbons can not be converted soon, the same would be discharged from the reaction system along with the alkylate oil product continuously, and this will result in not only the higher content of the halogenated hydrocarbons in the alkylate oil, but also the loss of Brönsted acid from the ionic liquid and even the deactivation of the catalyst. In order to reduce the consumption of B acid for producing alkylate oil and the content of the halogenated hydrocarbons in the alkylate oil product, the present invention provide a process which can effectively prolong the life of the ionic liquid catalyst and reduce the content of the halogenated hydrocarbons in the alkylate oil product, i.e. an alkylation process using ionic liquid as catalyst, wherein halogenated hydrocarbons-rich fraction is separated from the alkylate oil product by distillation or adsorption, and then the separated fraction is reintroduced into the reaction system.

According to the present invention, with the proviso that all the above mentioned requirements being in line with, said ionic liquid catalyst may be selected from various ionic liquids reported or known as catalysts for catalytic alkylation reactions, and said ionic liquids may be simple ones as above described, or composite ones, i.e. said ionic liquids may have an anion derived from two or more metallic compounds, of which at least one metallic compound is aluminum chloride or aluminum bromide and the other metallic compounds are halide, sulphate or nitrate of aluminium, copper, iron, zinc, nickel, titanium or silver. The ionic liquids may be selected, prepared and utilized as that in the prior art, and thus no further detailed description is provided herein. The above mentioned U.S. Pat. No. 7,285,698 and Chinese Patent CN 1500764A are incorporated herein by reference in their entirety.

According to the present invention, the alkylation reaction means the reactions between C4 alkane and C4 alkene, in particular the C4 alkylation reaction between isobutane and butene, i.e. the reaction feed is essentially a mixture of isobutane and C4 alkene (butene), wherein C4 alkene may comprise various iso- and n-alkenes such as 1-butene, 2-butene, iso-butene or mixture thereof. In practice, a hydrocarbon feed comprising C4 alkane and C4 alkene as major components may also be used, and the feed may also comprise propylene at a minor amount. The alkylation conditions and parameters may be those reported or used in the prior art. During the alkylation reaction, isobutane is generally present at an excessive amount and some alkanes with other carbon numbers such as propane, pentane etc. may also be present at a minor amount, i.e. the molar ratio between alkane and alkene in the reaction feed should be more than 1, generally 1:1-40:1; the reaction temperature may be in the range of −20 to 100, preferably in the range of 0 to 50; the reaction pressure should be selected so that the reaction feed could be maintained as liquids under the reaction conditions, and generally in the range of 0.1 to 1.6 MPa.

According to the present invention, reintroducing the halogenated hydrocarbons-rich fraction into the reaction system may comprise:

mixing the halogenated hydrocarbons-rich fraction with the reaction feed and then introducing the mixture into the reactor;

mixing the halogenated hydrocarbons-rich fraction with the ionic liquid catalyst and then introducing the mixture into the reactor;

introducing the halogenated hydrocarbons-rich fraction into the reactor directly; and/or mixing the halogenated hydrocarbons-rich fraction with the recycled C4 alkane and then introducing the mixture into the reactor.

Based on the researches, the present inventors have found that the halogenated hydrocarbons contained in the alkylate oil product are mostly mono-halogenated C3 to C5 hydrocarbons, especially mono-halogenated C4 hydrocarbons, and the boiling range of these halogenated hydrocarbons substantially corresponds to C5 to C7 fraction in the alkylation product, e.g. 2-chloropropane is with a boiling point of 35; 2-chloro-2-methyl propane is with a boiling point of 51; 1-chloro-2-methyl propane is with a boiling point of 69; 2-chloro-2-methyl butane is with a boiling point of 87, etc. Based on the distillation of the alkylation product, it can be known that the boiling range of C5 to C7 fraction is mainly of 28-99, and the boiling range of C6 fraction is mainly of 50-69. In the above process, therefore, the halogenated hydrocarbons-rich fraction may be determined as C5 to C7 fraction distilled from the alkylation product, more preferably as C6 fraction. During the reintroducing, mixing the separated fraction with the reaction feed and then introducing the mixture into the reactor is more favorable to prolong the life of acidic ionic liquid catalyst and improve the feed amount processed by per unit weight of the catalyst.

According to the present invention, the alkylation reaction system may comprise distillation column(s) or similar equipment to distill the alkylation product, i.e. distilling the alkylation product may comprise introducing the alkylation product into a distillation column, and then withdrawing the halogenated hydrocarbons-rich fraction from the distillation column as a sidedraw. Depending on the specific circumstances during the production, a single column or multiple columns may be arranged to distill the alkylation product. For example, the alkylation product may be introduced into a single distillation column, and then the halogenated hydrocarbons-rich fraction is withdrawn from this distillation column as a sidedraw and reintroduced into the reaction system; alternatively, the alkylation product may be introduced into two or more distillation columns in series, and then the halogenated hydrocarbons-rich fraction is withdrawn from the last distillation column as a sidedraw and reintroduced into the reaction system. Based on the requirements regarding the separated fraction, single sidedraw may be withdrawn; however, multiple sidedraws may also be withdrawn in order to obtain the fraction with a narrower boiling range such as C6 fraction.

According to the present invention, the halogenated hydrocarbons or halogenated hydrocarbons-rich fraction may be removed from the alkylation products and then reintroduced into the reaction system, i.e. the halogenated hydrocarbons-rich fraction may also be the fraction obtained by adsorbing the halogenated hydrocarbons from the alkylation product by an adsorption material and then desorbing the adsorbed halogenated hydrocarbons by C3 to C6 hydrocarbon material, the adsorption material comprises molecular sieve, activated carbon, activated alumina, porous silica gel, adsorption resin, activated carbon fiber, acid clay or any mixture thereof.

Due to the strong electronegativity of halogen, halogenated hydrocarbons are with a bigger polarity than the alkylate oil product. Based on the researches, the present inventor have further found that mono-halogenated C3 to C5 hydrocarbons contained in the alkylate oil product may be adsorbed therefrom by an adsorption material such as molecular sieve, activated carbon, activated alumina, porous silica gel, adsorption resin, activated carbon fiber, acid clay etc. or other material, which is capable of adsorbing halogenated hydrocarbons from the alkylate oil product, and then the adsorbed halogenated hydrocarbons may be desorbed by suitable light hydrocarbon fraction to obtain the light hydrocarbon fraction comprising halogenated hydrocarbons. Better adsorption and desorption effects may be achieved by selecting the adsorption materials suitably. As above mentioned, the light hydrocarbon fraction comprising halogenated hydrocarbons obtained after desorption may be referred as halogenated hydrocarbons-rich fraction too. According to the practical requirement, those skilled in the art can make chooses over the appropriate adsorption materials, which are capable of adsorbing halogenated hydrocarbons from the alkylate oil product and of which the preferred is molecular sieve and activated alumina.

According to the present invention, the hydrocarbon material (light hydrocarbon) used as the desorbing agent may be C3 to C6 alkanes or mixtures thereof, such as propane, butane, isobutane, C5 alkanes, C6 alkanes and mixture thereof, of which isobutane is preferred with consideration about the practical production. The C3 to C6 light hydrocarbons may be introduced from external sources, or may be fractions distilled from the alkylation product, e.g. a part of the isobutane, distilled from the alkylation product and recycled, may be directly introduced into the adsorption system and bring the desorbed halogenated hydrocarbons back to the reaction system.

According to the present invention, the adsorption-desorption of the alkylation product may comprise firstly introducing the separated alkylate oil product into the adsorption unit with an adsorption material arranged therein previously, and passing the light hydrocarbon fraction as the desorbing agent such as the recycled alkane (isobutane) into the adsorption unit to desorb the halogenated hydrocarbons and then bring the desorbed halogenated hydrocarbons back to the reaction system.

The above mentioned adsorption-desorption may also be combined with the distillation, wherein the halogenated hydrocarbons-rich fraction (C5 to C7 fraction) withdrawn as sidedraw from the distillation column is firstly introduced into the adsorption unit and then the halogenated hydrocarbons are brought into the alkylation reaction system after being desorbed.

According to the present invention, by reintroducing the halogenated hydrocarbons-rich fraction from the alkylation product into the reaction system, the process can effectively prolong the life of the acidic ionic liquid catalyst, reduce the consumption of B acid and improve the performance of the catalyst, so as to improve the feed amount processed by per unit weight of the catalyst significantly, and can effectively reduce the content of halogenated hydrocarbons in the alkylate oil too due to the separation of the halogenated hydrocarbons from the alkylation product.

According to the present invention, depending on the specifically selected ionic liquid catalysts, the halogenated hydrocarbons collected by distillation and/or adsorption are mainly chlorohydrocarbon or bromohydrocarbon.

As above mentioned, according to the present invention, reintroducing the halogenated hydrocarbons-rich fraction into the reaction system may comprise mixing the halogenated hydrocarbons-rich fraction with the reaction feed and then introducing the mixture into the reactor; mixing the halogenated hydrocarbons-rich fraction with the ionic liquid catalyst and then introducing the mixture into the reactor; introducing the halogenated hydrocarbons-rich fraction into the reactor directly; or mixing the halogenated hydrocarbons-rich fraction with the recycled isobutane and then introducing the mixture into the reactor. It is important that the present invention provides an improved process for producing alkylate oil using an acidic ionic liquid as the catalyst, wherein the halogenated hydrocarbons in the alkylation products being brought into the alkylation reaction system as fraction, so as to compensate the consumption of B acid of the acidic ionic liquid and prolong the life of the acidic ionic liquid catalyst; furthermore, wherein the amount of the halogenated hydrocarbons or halogenated hydrocarbons-rich fraction to be reintroduced is determined by the recycle of the reaction system, so as to facilitate the industrial practices. On the other hand, when putting the present invention into practices, the alkylation reaction apparatuses in the prior art may be used with some appropriate modifications such as addition of sidedraw(s) to the distillation column for separating isobutane from alkylate oil, addition of adsorption unit, and addition of pipes for passing the separated fraction to the reaction system, i.e. the inventive process can improve the efficiency of the alkylation reaction without paying much equipment investment.

In general, according to the present invention, the process can effectively prolong the life of the acidic ionic liquid catalyst, reduce the consumption of B acid in the alkylation reaction, and reduce the halogen content in the alkylate oil without compromising the quality thereof. The process according to the present invention may be operated simply, so that may be industrialized easily.

In addition, according to the present invention, a process for producing alkylate oil is provided, wherein the alkylate oil comprises halogen-containing compounds, in particular halogenated hydrocarbons at a reduced amount. This alkylate oil comprising halogenated hydrocarbons at a reduced amount is especially suitable for use as fuel or fuel blending component, which may be optionally further processed to remove at least a part of the residual halogenated hydrocarbons prior to use. According to the present invention, the halogenated hydrocarbons are reintroduced into the reaction system, however, the halogenated hydrocarbons may also be removed from the process and disposed subsequently or used in other processes.

DETAILED DESCRIPTION

Now the present invention and its advantageous effects will be further illustrated by following examples, which should not be construed as limitations to the scope of the present invention.

Figure 1:
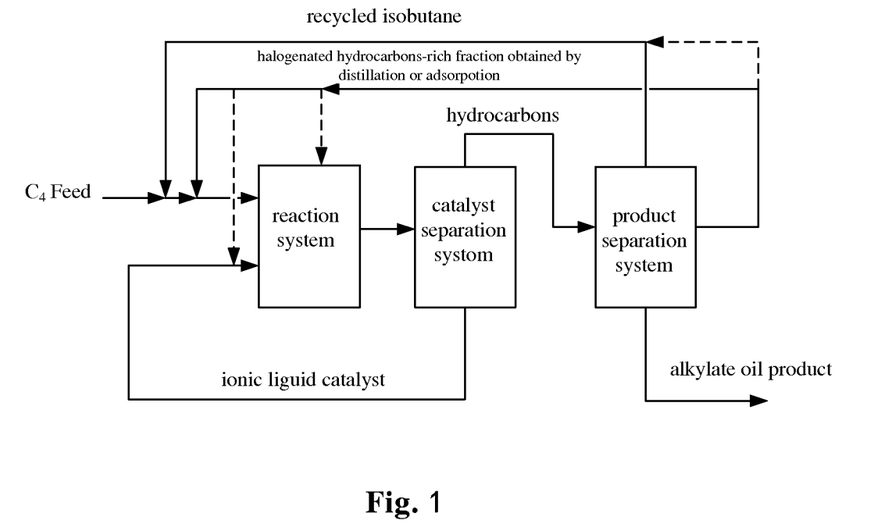
FIG. 1 is a schematic representative depicting the process for producing alkylate oil by alkylation reaction according to the present invention.

FIG. 1 is a schematic representative depicting the alkylation process according to the present invention, wherein C4 feed being alkylated in the presence of the ionic liquid as catalyst in the reaction system, and the alkylation product being separated from the catalyst in the catalyst separation system (also referred as the separation system) and then being introduced into the product separation system, and the separated ionic liquid catalyst being brought back to the reaction system. In the product separation system (single distillation column or multiple distillation columns), excessive C4 alkane (isobutane) being recycled to the feed inlet, and the alkylate oil being discharged and collected. The above mentioned is the conventional alkylation reaction procedure. Based on this conventional procedure, the process according to the present invention further comprises obtaining the halogenated hydrocarbons-rich fraction from the product separation system and reintroducing the separated fraction into the reaction system. As shown in FIG. 1, separating the halogenated hydrocarbons-rich fraction as a sidedraw from the distillation column and reintroducing the separated fraction into the reaction system may comprise mixing the separated fraction with the reaction feed and then introducing the mixture into the reaction system, introducing the separated fraction into the reaction system directly, mixing the separated fraction with the ionic liquid catalyst and then introducing the mixture into the reaction system, as well as mixing the separated fraction with the recycled isobutane and then introducing the mixture into the reaction system.

However, FIG. 1 does not cover all the embodiments according to the present invention yet in this regard, and the halogenated hydrocarbons-rich fraction to be reintroduced may also be obtained by adsorbing the alkylate oil coming from the product separation system and then desorbing. The more specific embodiments may refer to the following examples with reference to FIGS. 2 to 6.

All the acidic ionic liquid catalysts used in the examples are prepared according to the processes described in U.S. Pat. No. 7,285,698, USP 20040133056A1 and CN 02149296.4 or purchased commercially. In the examples, the composition of the alkylation product is determined by Gas Chromatograph, the halogen (chloro- or bromo-) in the alkylation product is quantitively analyzed by Micro-Coulomb method, and the activity of the catalysts is evaluated on butene conversion. The butene conversion is defined as following: butene conversion=((the initial butene mass−the butene mass after reaction)/the initial butene mass)×100%.

Comparative Example

Catalytic alkylation reaction of isobutane is carried out in a continuous apparatus using an acidic ionic liquid as catalyst, wherein the cation is provided by $Et_3NHCl$ and the anion is provided by $AlCl_3$ and CuCl. The inventory of the ionic liquid is of 20 kg. The reaction pressure is 0.5 MPa and the reaction temperature is 30° C. The feed is a mixture of isobutane and 2-butene with a molar ratio between alkane and alkene of 20:1. Collecting the alkylation product obtained from the catalytic alkylation reaction by fresh catalyst and analyzing composition thereof, and the results are shown in Table 1. Of the results, the ratio of TMP/DMH shows the quality of the alkylate oil, and the higher the ratio, the better the quality of the alkylate oil.

As can be seen from Table 1, when the amount of the processed feed is up to 1000 kg, i.e. the feed processed by per gram of the ionic liquid catalyst is up to 50 g, the catalyst activity declines significantly. When the amount of processed feed is up to 1200 kg, i.e. the feed processed by per gram of the ionic liquid catalyst is up to 60 g, the butene conversion is almost of 0, which indicates that the B acid is totally lost from the catalyst, i.e. the catalyst gets deactivated totally.

TABLE 1

Life test on catalytic alkylation by ionic liquid

| Processed feed, g/g ionic liquid | Butene conversion, % | Selectivity of C8 fraction, wt % | TMP/DMH |
|---|---|---|---|
| 10 | 100 | 88 | 14 |
| 20 | 100 | 89 | 15 |
| 30 | 100 | 89 | 15 |
| 40 | 100 | 89 | 15 |
| 50 | 76 | 83 | 13 |
| 60 | 0 | — | — |

The alkylation product obtained in above test is of 110 kg in all.

80 kg the above alkylation product is distilled to get 8.8 kg C5~C7 fraction. The chlorine contents in the alkylation product before and after distillation are determined and shown in Table 2. The results show that the chlorine contents in C8 and C8+ fractions after distillation are very low, thus these fractions may be used as alkylate oil products, but the chlorine content in C5 to C7 fraction is very high, which indicates the halogenated hydrocarbons in the alkylation product are mainly present in this fraction.

TABLE 2

Chlorine contents in alkylation product before and after distillation

| Fraction | chlorine content, mg/L | Percent of fraction, wt % |
|---|---|---|
| Full range fraction | 344 | 100.0 |
| C5~C7 fraction | 1868 | 11.0 |
| C8+ fraction | 10 | 89.0 |

From 30 kg the above alkylation product chlorine is removed by adsorption with 13× molecular sieve, so that the alkylate oil has a chlorine content of 8 mg/L; then the molecular sieve is desorbed with isobutane at 110° C., and 10 kg isobutane with chlorine content of 989 mg/L is obtained after condensation.

Example 1

Catalytic alkylation reaction of isobutane is carried out in a continuous apparatus using the same acidic ionic liquid as catalyst as that in the comparative example. The inventory of the ionic liquid is of 200 g. The reaction pressure is 0.5 MPa and the reaction temperature is 30. The feed is the same mixture of isobutane and 2-butene with a molar ratio between alkane and alkene of 20:1 as that in the comparative example. Mixing 200 g C5 to C7 fraction obtained in the comparative example with 100 kg feed, conducting the alkylation reaction continuously, collecting the alkylate oil products through separating out isobutane and catalyst (the same in the following examples), and analyzing the composition thereof. The results are shown in Table 3.

TABLE 3

Life test on catalytic alkylation by ionic liquid

| Processed feed, g/g ionic liquid | Butene conversion, % | Selectivity of C8 fraction, wt % | TMP/DMH |
|---|---|---|---|
| 20 | 100 | 87 | 14 |
| 40 | 100 | 88 | 15 |
| 60 | 100 | 88 | 15 |
| 80 | 100 | 88 | 15 |
| 100 | 100 | 88 | 15 |
| 120 | 84 | 81 | 13 |
| 140 | 0 | — | — |

As can be seen from Table 3, when the amount of the processed feed is up to 24 kg, i.e. the feed processed by per gram of the ionic liquid catalyst is up to 120 g, the catalyst activity declines significantly. When the amount of the processed feed is up to 28 kg, i.e. the feed processed by per gram of the ionic liquid catalyst is up to 140 g, the butene conversion is almost of 0, which indicates the catalyst gets deactivated totally. When the catalyst is with a normal activity, the obtained alkylation product has the selectivity of C8 fraction and the ratio of TMP/DMH comparable to that in the comparative example. The obtained alkylate oil is distilled and the chlorine content in the separated C8+ fraction is determined to be of 8.9 mg/L. It can be seen that, compared with the comparative example, mixing the feed with C5 to C7 fraction having a higher chlorine content from the alkylate oil product may prolong the life of the ionic liquid catalyst significantly without compromising the quality of the alkylate oil product substantially.

C5 to C7 fraction distilled from the alkylate oil may be reintroduced into the reaction system to conduct the alkylation reaction continuously.

Example 2

Catalytic alkylation reaction of isobutane is carried out in a continuous apparatus using the same acidic ionic liquid as catalyst as that in the comparative example. The inventory of the ionic liquid is of 200 g. The reaction pressure is 0.5 MPa and the reaction temperature is 30. The feed is the same mixture of isobutane and 2-butene with a molar ratio between alkane and alkene of 20:1 as that in the comparative example. Mixing 200 g C5 to C7 fraction obtained in the comparative example with 200 g ionic liquid catalyst, and conducting the alkylation reaction continuously to obtain the alkylate oil product and then analyze the composition thereof. The results are shown in Table 4.

TABLE 4

Life test on catalytic alkylation by ionic liquid

| Processed feed, g/g ionic liquid | Butene conversion, % | Selectivity of C8 fraction, wt % | TMP/DMH |
|---|---|---|---|
| 20 | 100 | 87 | 14 |
| 40 | 100 | 87 | 15 |
| 60 | 100 | 89 | 15 |
| 80 | 100 | 89 | 15 |
| 100 | 100 | 88 | 14 |
| 120 | 79 | 82 | 12 |
| 140 | 0 | — | — |

As can be seen from Table 4, when the amount of the processed feed is up to 24 kg, i.e. the feed processed by per gram of the ionic liquid catalyst is up to 120 g, the catalyst activity declines significantly. When the amount of the processed feed is up to 28 kg, i.e. the feed processed by per gram of the ionic liquid catalyst is up to 140 g, the butene conversion is almost of 0, which indicates the catalyst gets deactivated totally. When the catalyst is with a normal activity, the obtained alkylation product has the selectivity of C8 fraction and the ratio of TMP/DMH comparable to that in the comparative example. The obtained alkylate oil is distilled and the chlorine content in the separated C8+ fraction is determined to be of 9.2 mg/L. It can be seen that, compared with the comparative example, pre-mixing the ionic liquid with C5 to C7 fraction having a higher chlorine content from the alkylate oil product may also prolong the life of the ionic liquid catalyst significantly without compromising the quality of the alkylate oil product substantially.

C5 to C7 fraction distilled from the alkylate oil may be reintroduced into the reaction system to conduct the alkylation reaction continuously.

Example 3

Catalytic alkylation reaction of isobutane is carried out in a continuous apparatus using the same acidic ionic liquid as catalyst as that in the comparative example. The inventory of the ionic liquid is of 200 g. The reaction pressure is 0.5 MPa and the reaction temperature is 30. The feed is the same mixture of isobutane and 2-butene with a molar ratio between alkane and alkene of 20:1 as that in the comparative example. The flowrate of the feed is 500 g/h. Introducing C5 to C7 fraction obtained in the comparative example into the reactor directly at a flowrate of 4 g/h, and conducting the alkylation reaction continuously. Separating and collecting the alkylate oil product, and analyzing the composition thereof. The results are shown in Table 5.

TABLE 5

Life test on catalytic alkylation by ionic liquid

| Processed feed, g/g ionic liquid | Butene conversion, % | Selectivity of C8 fraction, wt % | TMP/DMH |
|---|---|---|---|
| 20 | 100 | 86 | 14 |
| 40 | 100 | 88 | 15 |
| 60 | 100 | 88 | 15 |
| 80 | 100 | 88 | 15 |
| 100 | 100 | 88 | 15 |
| 120 | 89 | 84 | 13 |
| 140 | 0 | — | — |

As can be seen from Table 5, when the amount of the processed feed is up to 24 kg, i.e. the feed processed by per gram of the ionic liquid catalyst is up to 120 g, the catalyst activity declines significantly. When the amount of the processed feed is up to 28 kg, i.e. the feed processed by per gram of the ionic liquid catalyst is up to 140 g, the butene conversion is almost of 0, which indicates the catalyst gets deactivated totally. When the catalyst is with a normal activity, the obtained alkylation product has the selectivity of C8 fraction and the ratio of TMP/DMH comparable to that in the comparative example. The obtained alkylate oil is distilled and the chlorine content in the separated C8+ fraction is determined to be of 9.1 mg/L. It can be seen that, compared with the comparative example, introducing C5 to C7 fraction having a higher chlorine content from the alkylate oil product into the reactor directly may also prolong the life of the ionic liquid catalyst significantly without compromising the quality of the alkylate oil product substantially.

Example 4

Catalytic alkylation reaction of isobutane is carried out in a continuous apparatus using the same acidic ionic liquid as catalyst as that in the comparative example. The inventory of the ionic liquid is of 200 g. The reaction pressure is 0.5 MPa and the reaction temperature is 30. The feed is the same mixture of isobutane and 2-butene with a molar ratio between alkane and alkene of 20:1 as that in the comparative example. The flowrate of the feed is 500 g/h. The isobutane obtained in the comparative example is firstly mixed with the feed at a flowrate of 8 g/h, and then introduced into the reaction system to conduct the alkylation reaction by the ionic liquid to obtain the alkylation product. The composition of the alkylation product is analyzed and the results are shown in Table 6.

TABLE 6

Life test on catalytic alkylation by ionic liquid

| Processed feed, g/g ionic liquid | Butene conversion, % | Selectivity of C8 fraction, wt % | TMP/DMH |
| --- | --- | --- | --- |
| 20 | 100 | 88 | 14 |
| 40 | 100 | 89 | 15 |
| 60 | 100 | 89 | 16 |
| 80 | 100 | 88 | 15 |
| 100 | 100 | 89 | 15 |
| 120 | 92 | 87 | 13 |
| 140 | 27 | 63 | 3 |

As can be seen from Table 6, when the amount of the processed feed is up to 24 kg, i.e. the feed processed by per gram of the ionic liquid catalyst is up to 120 g, the catalyst activity declines significantly. When the amount of the processed feed is up to 28 kg, i.e. the feed processed by per gram of the ionic liquid catalyst is up to 140 g, the butene conversion is of 27% only, which indicates the catalyst gets deactivated substantially. When the catalyst is with a normal activity, the obtained alkylation product has the selectivity of C8 fraction and the ratio of TMP/DMH comparable to that in the comparative example. The obtained alkylate oil is distilled and the chlorine content in the separated C8+ fraction is determined to be of 9.2 mg/L. It can be seen that, compared with the comparative example, firstly mixing the feed with C5 to C7 fraction having a higher chlorine content from the alkylate oil product and then introducing the mixture into the reaction system may also prolong the life of the ionic liquid catalyst significantly without compromising the quality of the alkylate oil product substantially.

Example 5

A continuous alkylation reaction is carried out following the alkylation reaction process by the ionic liquid shown in FIG. 1 based on the scheme of Example 1. The reaction feed (referred as C4 feed in the figure) and the ionic liquid are introduced into the reactor simultaneously to establish the alkylation reaction system. The alkylation product is introduced into the separation system, wherein the ionic liquid is separated and then recycled to the reaction system, and the alkylation product is passed to a distillation column subsequently. C5 to C7 fraction or C6 fraction, i.e. the halogenated hydrocarbons-rich fraction, is withdrawn from the distillation column as a sidedraw by controlling the distillation operation, and reintroduced into to the reactor by mixing into the reaction feed. At the same time, n-butane is separated from the distillation column as a sidedraw and alkylate oil is discharged at the bottom of the distillation column, both of these streams are sent into the product storage tanks respectively. Excessive isobutane separated from the top of the distillation column is recycled to the reactor to be utilized furthermore. The alkylation reaction conditions are same as that in Example 1 except that C5 to C7 fraction is distilled continuously from the alkylation product by a single distillation column as a sidedraw and then reintroduced into the reaction feed to conduct the reaction continuously.

By comparing the comparative example and Example 1, it can be anticipated obviously that producing alkylate oil by the alkylation reaction following the process in FIG. 1 can not only prolong the life of the ionic liquid catalyst, but also reduce the chlorine content in the alkylate oil product.

Example 6

Figure 2:
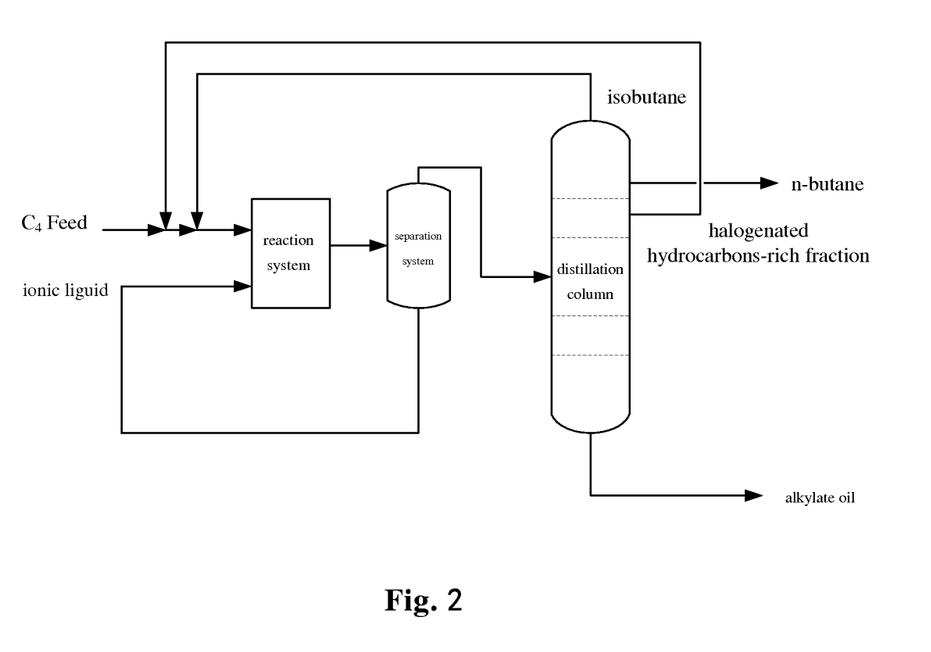
FIG. 2 is a schematic representative depicting an embodiment of the process for producing alkylate oil by alkylation reaction according to the present invention, wherein halogenated hydrocarbons-rich fraction distilled from the alkylation product being mixed into the reaction feed and then introduced into the reactor.

The alkylation reaction process by the ionic liquid shown in FIG. 2 is employed based on the scheme of Example 2. The specific embodiment is a catalytic alkylation reaction process by the ionic liquid using a single distillation column, wherein the excessive isobutane separated from the top of the distillation column is recycled, the alkylate oil product is discharged at the bottom of the distillation column, and C5 to C7 fraction or C6 fraction (the halogenated hydrocarbons-rich fraction) is withdrawn from the distillation column as a sidedraw and then pre-mixed with the ionic liquid catalyst recycled from the catalyst separation system to back to the reaction system. The alkylation reaction conditions are same as that in Example 2 except that C5 to C7 fraction is distilled continuously from the alkylation product by a single distillation column as sidedraw and then mixed with the ionic liquid catalyst and reintroduced into the reaction feed to conduct the reaction continuously.

By comparing the comparative example and Example 2, it can be anticipated obviously that producing alkylate oil by the alkylation reaction following the process in FIG. 2 can not only prolong the life of the ionic liquid catalyst, but also reduce the chlorine content in the alkylate oil product.

As a variation of the process, controlling the distillation conditions and multiple sidedraws being set with the distillation column, C6 fraction is collected and reintroduced in the same way, and C5 fraction is collected at the same time, which may be used as alkylate oil product together with the bottom fraction or otherwise based on the design requirements.

Example 7

Figure 3:
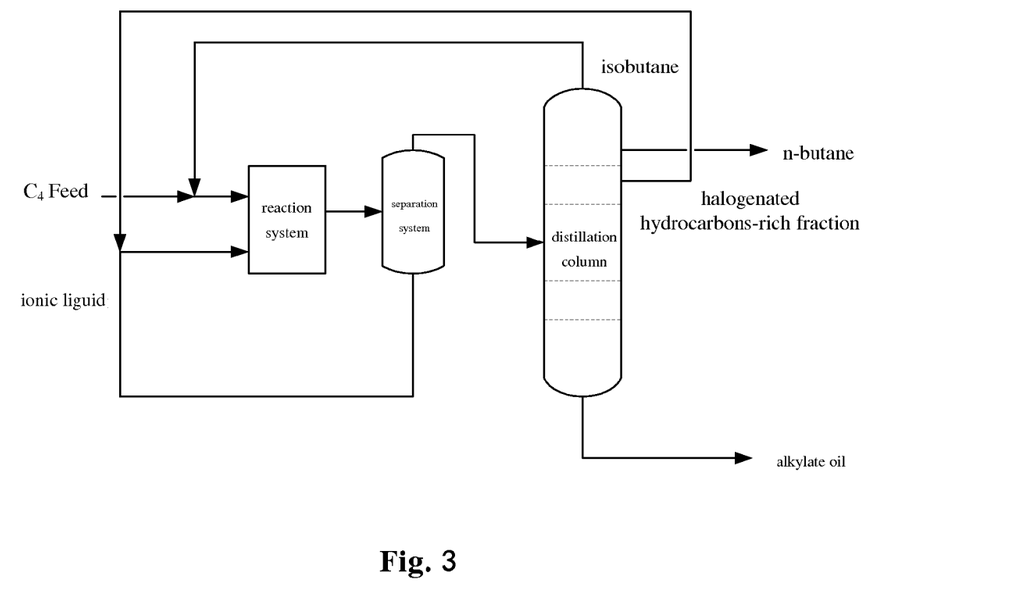
FIG. 3 is a schematic representative depicting another embodiment of the process for producing alkylate oil by alkylation reaction according to the present invention, wherein halogenated hydrocarbons-rich fraction distilled from the alkylation product being firstly mixed into the ionic liquid catalyst and then introduced into the reactor.

The alkylation reaction process by the ionic liquid shown in FIG. 3 is employed based on the scheme of Example 3. In the catalytic alkylation reaction process by the ionic liquid using a single distillation column, the excessive isobutane separated from the top of the distillation column is recycled, the alkylate oil product is discharged at the bottom of the distillation column, and the halogenated hydrocarbons-rich fraction (C5 to C7 fraction) is withdrawn from the distillation column as a sidedraw and reintroduced directly into the reactor to be used in the alkylation reaction. The alkylation reaction conditions are same as that in Example 3 except that C5 to C7 fraction is distilled continuously from the alkylation product by a single distillation column as a sidedraw and then reintroduced into the reactor directly to conduct the reaction continuously.

By comparing the comparative example and Example 3, it can be anticipated obviously that producing alkylate oil by the alkylation reaction following the process in FIG. 3 can not only prolong the life of the ionic liquid catalyst, but also reduce the chlorine content in the alkylate oil product.

Example 8

Figure 4:
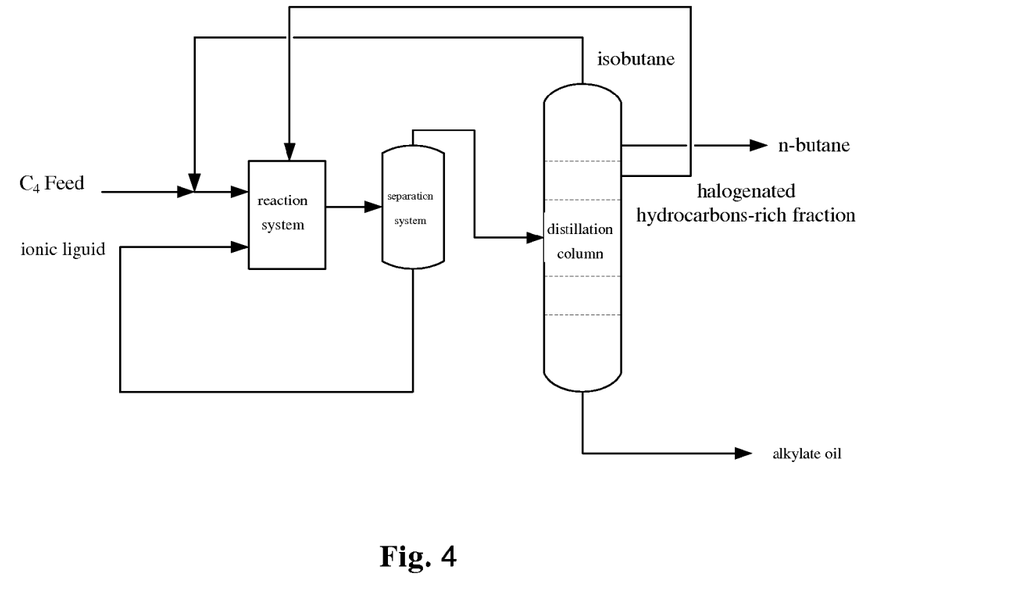
FIG. 4 is a schematic representative depicting another embodiment of the process for producing alkylate oil by alkylation reaction according to the present invention, wherein halogenated hydrocarbons-rich fraction distilled from the alkylation product being introduced into the reactor directly.

The alkylation reaction process by the ionic liquid shown in FIG. 4 is employed based on the scheme of Example 5 with some variations. In the catalytic alkylation reaction process by the ionic liquid using multiple distillation columns (two staged separation), two distillation columns A and B are set in series, wherein the excessive isobutane is separated from the top of distillation column A and recycled, the bottom fraction of distillation column A is sent into distillation column B, n-butane is separated from the top of distillation column B, and C5 fraction and C6 fraction is withdrawn from distillation column B as sidedraws respectively, of which C5 fraction is used as the alkylate oil product together with the bottom fraction, and C6 fraction is pre-mixed with the reaction feed and then reintroduced into the reaction system. The alkylation reaction conditions are same as that in Example 1 except that C5 to C7 fraction is distilled continuously from the alkylation product by multiple distillation columns as a sidedraw and then reintroduced into the reaction feed to conduct the reaction continuously.

Based on Examples 1 and 5, it can be anticipated obviously that reintroducing C6 fraction with the most concentrated halogenated hydrocarbons into the reaction system as in this Example can not only prolong the life of ionic liquid catalyst, but also reduce the chlorine content in the alkylate oil product and at the same time increase the production of the alkylate oil.

Example 9

Figure 5:
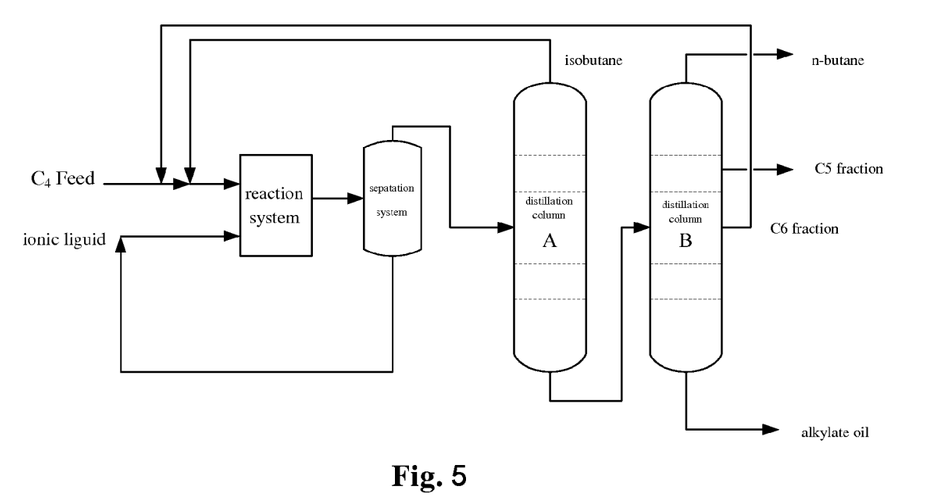
FIG. 5 is a schematic representative depicting another embodiment of the process for producing alkylate oil by alkylation reaction according to the present invention, wherein the alkylation product being distilled by multiple columns with multiple sidedraws, and the distilled C6 fraction being mixed into the reaction feed and then introduced into the reactor.

The alkylation reaction process by the ionic liquid shown in FIG. 5 is employed based on the scheme of Example 4. The specific embodiment is a catalytic alkylation reaction process by the ionic liquid using a single distillation column, wherein the excessive isobutane separated from the top of the distillation column is partly recycled to the reaction feed, and the bottom fraction is the alkylate oil, which is introduced into adsorption drums A/B, wherein an adsorption material such as 13× molecular sieves, NaY zeolite or activated alumina is arranged previously, to remove halogenated hydrocarbons by adsorption. The adsorption drum with saturated adsorption material is regenerated through desorption by the not-recycled part of the separated isobutane from the distillation column. After being cooled, the isobutane with the desorbed halogenated hydrocarbons is also mixed with the reaction feed and then reintroduced into the reaction system to conduct the alkylation reaction. The alkylate oil after desorption of halogenated hydrocarbons is discharged as the product. The alkylation reaction conditions are same as that in example 4.

Based on the comparative example, Examples 1 and 4, it can be anticipated obviously that producing alkylate oil by the alkylation reaction following the process in FIG. 5 can not only prolong the life of the ionic liquid catalyst, but also reduce the chlorine content in the alkylate oil product.

Example 10

Figure 6:
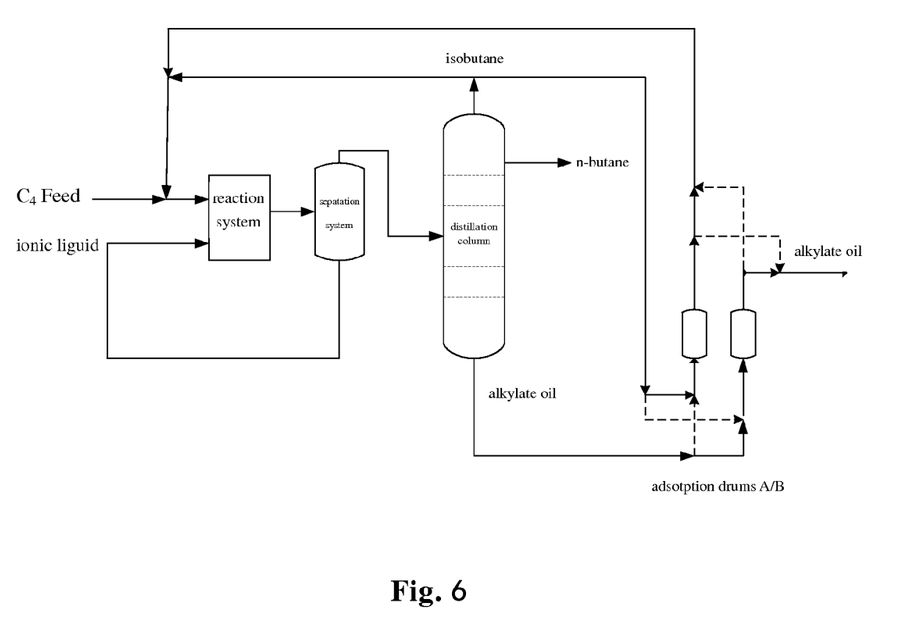
FIG. 6 is a schematic representative depicting another embodiment of the process for producing alkylate oil by alkylation reaction according to the present invention, wherein the halogenated hydrocarbons being separated from the alkylate oil by adsorption and reintroduced into the reaction system.
Figure 7:
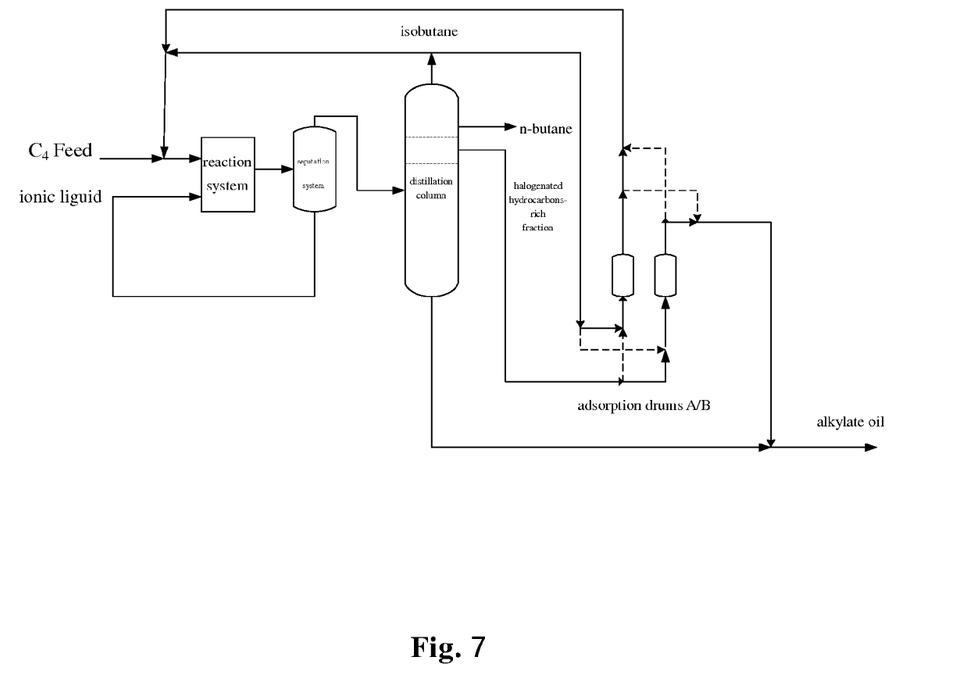
FIG. 7 is a schematic representative depicting another embodiment of the process for producing alkylate oil by alkylation reaction according to the present invention, wherein distillation and adsorption being used in combination.

The alkylation reaction process by the ionic liquid shown in FIG. 6 is employed based on the scheme of Example 4. The specific embodiment is a catalytic alkylation reaction process by the ionic liquid using a single distillation column, wherein the excessive isobutane separated from the top of the distillation column is partly recycled to the reaction feed, the bottom fraction is the alkylate oil product, and the halogenated hydrocarbons-rich C6 to C7 fraction and n-butane are withdrawn from the distillation column as sidedraws, of which the halogenated hydrocarbons-rich fraction is introduced into adsorption drums A/B to remove the halogenated hydrocarbon by adsorption. The fraction after desorption of halogenated hydrocarbon is combined with the bottom fraction and discharged from the system as the alkylate oil product. The adsorption drum with saturated adsorption material is regenerated through desorption by the not-recycled part of the separated isobutane from the distillation column. After being cooled, the isobutane with the desorbed halogenated hydrocarbons is mixed with the reaction feed and then reintroduced into the reaction system to conduct the alkylation reaction. The alkylation reaction conditions are same as that in Example 4.

Based on the comparative example, Examples 1 and 4, it can be anticipated obviously that producing alkylate oil by the alkylation reaction following the process in FIG. 6 can not only prolong the life of the ionic liquid catalyst, but also reduce the chlorine content in the alkylate oil product.

Finally, it should be noted that all the above examples are intend to illustrate the technical solutions of the present invention only and should not be construed as limitations to the scope of the present invention. All of the modification or equivalents of the technical solutions of the embodiments of the present invention disclosed herein made by those skilled in the art should fall into the scope of the present invention as claimed in the appended claims.

What is claimed is:

1. An alkylation process for producing alkylate oil using ionic liquid as catalyst, wherein during the alkylation reaction the reaction feed is a mixture of C4 alkene and C4 alkane with C4 alkane being at an excessive amount and then separated from the alkylation product and recycled, and the process further comprises separating halogenated hydrocarbons-rich fraction from the alkylation product and reintroducing the separated fraction into the reaction system during the alkylation reaction, and the ionic liquid catalyst used in the alkylation reaction has a cation derived from hydrohalide of alkyl amine, hydrohalide of imidazole or hydrohalide of pyridine and an anion derived from one or more metallic compounds.

2. The process according to claim 1, wherein said process comprises separating halogenated hydrocarbons-rich fraction from the alkylation product by distillation and/or adsorption and reintroducing the separated fraction into the reaction system during the alkylation reaction.

3. The process according to claim 1, wherein said halogenated hydrocarbons-rich fraction is C5 to C7 fraction distilled from the alkylation product.

4. The process according to claim 1, wherein said halogenated hydrocarbons-rich fraction is obtained by adsorbing the halogenated hydrocarbons from the alkylation product by an adsorption material and then desorbing the adsorbed halogenated hydrocarbons by C3 to C6 hydrocarbon material, wherein the adsorption material comprises molecular sieve, activated carbon, activated alumina, porous silica gel, adsorption resin, activated carbon fiber, acid clay or any mixture thereof.

5. The process according to claim 1, wherein reintroducing the halogenated hydrocarbons-rich fraction into the reaction system comprises:
  mixing the halogenated hydrocarbons-rich fraction with the reaction feed and then introducing the mixture into the reactor;
  mixing the halogenated hydrocarbons-rich fraction with the ionic liquid catalyst and then introducing the mixture into the reactor;
  introducing the halogenated hydrocarbons-rich fraction into the reactor directly; and/or
  mixing the halogenated hydrocarbons-rich fraction with the recycled C4 alkane and then introducing the mixture into the reactor.

6. The process according to claim 3, wherein distilling the alkylation product comprises introducing the alkylation product into a distillation column, and then withdrawing the halogenated hydrocarbons-rich fraction from the distillation column as a sidedraw.

7. The process according to claim 6, wherein the alkylation product is introduced into a single distillation column, and then the halogenated hydrocarbons-rich fraction is withdrawn from this distillation column as a sidedraw and reintroduced into the reaction system; alternatively, the alkylation product is introduced into two or more distillation columns in series, and then the halogenated hydrocarbons-rich fraction is withdrawn from the last distillation column as a sidedraw and reintroduced into the reaction system.

8. The process according to claim 4, wherein adsorbing the halogenated hydrocarbons from the alkylation product by an adsorption material and then desorbing the adsorbed halogenated hydrocarbons by C3 to C6 hydrocarbon material comprises introducing the alkylation product into a distillation column, withdrawing the halogenated hydrocarbons-rich fraction from the distillation column as a sidedraw, adsorbing the halogenated hydrocarbons by an adsorption material, and/or introducing the alkylation product into a distillation column, adsorbing the halogenated hydrocarbons from the alkylate oil obtained at the bottom of the distillation column; and then desorbing the adsorbed halogenated hydrocarbons by a hydrocarbon material.

9. The process according to claim 4, wherein the C3 to C6 hydrocarbon material is C3 to C6 alkanes or mixture thereof.

10. The process according to claim 9, wherein the C3 to C6 hydrocarbon material is distilled from the alkylation product.

11. The process according to claim 1, wherein the ionic liquid has an anion derived from two or more metallic compounds, of which at least one metallic compound is aluminum chloride or aluminum bromide and the other metallic compound(s) are halide, sulphate or nitrate of aluminium, copper, iron, zinc, nickel, titanium or silver.

12. The process according to claim 1, wherein in the reaction feed, C4 alkane is isobutane and C4 alkene is 1-butene, 2-butene, iso-butene or any mixture thereof.

* * * * *